US011478265B2

(12) United States Patent
Lowe et al.

(10) Patent No.: US 11,478,265 B2
(45) Date of Patent: Oct. 25, 2022

(54) SURGICAL INSTRUMENT

(71) Applicant: Scanlan International, Inc., St. Paul, MN (US)

(72) Inventors: Patrick J. Lowe, Forest Lake, MN (US); Kelsey K. Sievert, Lakeland, MN (US); Sherri L. Baack, St. Paul, MN (US)

(73) Assignee: Scanlan International, Inc., St. Paul, MN (US)

( * ) Notice: Subject to any disclaimer, the term of this patent is extended or adjusted under 35 U.S.C. 154(b) by 340 days.

(21) Appl. No.: 16/748,120

(22) Filed: Jan. 21, 2020

(65) Prior Publication Data

US 2020/0229840 A1 Jul. 23, 2020

Related U.S. Application Data

(60) Provisional application No. 62/795,645, filed on Jan. 23, 2019.

(51) Int. Cl.
*A61B 17/32* (2006.01)
*A61B 17/3201* (2006.01)
*A61B 17/00* (2006.01)

(52) U.S. Cl.
CPC .. *A61B 17/320016* (2013.01); *A61B 17/3201* (2013.01); *A61B 2017/00424* (2013.01); *A61B 2217/002* (2013.01)

(58) Field of Classification Search
CPC ........ A61B 17/320016; A61B 17/3201; A61B 17/44; A61B 17/28; A61B 17/2816; A61B 17/282; A61B 17/2804; A61B 17/2841; A61B 17/285; A61B 17/2909; A61B 17/29; A61B 2017/00424; A61B 2017/2906; A61B 2017/2829; A61B 2017/2845; A61B 2017/2908; A61B 2017/2912–2916; A61B 2017/2919; A61B 2017/2922; A61B 2017/2926; A61B 2017/2933;

(Continued)

(56) References Cited

U.S. PATENT DOCUMENTS 5,308,357 A 5/1994 Lichtman
5,827,263 A * 10/1998 Furnish .............. A61B 17/2909
606/1
10,519,677 B2 * 12/2019 Fujii ..................... E04G 21/123

(Continued)

FOREIGN PATENT DOCUMENTS

WO 2017/042791 A2 3/2017

OTHER PUBLICATIONS

International Search Report and Written Opinion received for PCT Patent Application No. PCT/US2020/014386, dated Mar. 19, 2020, 11 pages.

*Primary Examiner* — Erich G Herbermann

(57) ABSTRACT

A surgical instrument including one or both of a shield on a distal end portion of a shaft and a counterweight in a handle for enhanced functionality, efficiency and/or efficacy. The shield covers portions of a linkage that extend beyond outer dimensions of the shaft during operation of the instrument. The counterweight is proximal to a hand grip and configured to locate a center of gravity of the instrument within the hand grip. The instrument may be configured as a video-assisted thoracoscopic (VATS) and/or minimally invasive cardiac surgery (MICS) device.

20 Claims, 2 Drawing Sheets

(58) Field of Classification Search
CPC .... A61B 2017/2939; A61B 2017/2947; A61B 2217/002; A61B 10/02; A61B 10/04
See application file for complete search history.

(56) References Cited

U.S. PATENT DOCUMENTS

| | | | |
|---|---|---|---|
| 10,537,348 B2* | 1/2020 | Rodriguez-Navarro | ..................... A61B 17/10 |
| 2006/0041274 A1* | 2/2006 | Su | .......................... A61B 17/29 606/205 |
| 2008/0029575 A1 | 2/2008 | Shelton et al. | |
| 2010/0004677 A1* | 1/2010 | Brostoff | ............. A61B 17/2909 606/205 |
| 2011/0184405 A1* | 7/2011 | Mueller | ............. A61B 18/1445 606/41 |
| 2011/0238064 A1 | 9/2011 | Williams | |
| 2012/0303021 A1* | 11/2012 | Guerra | ............... A61B 18/1445 606/41 |
| 2017/0231624 A1 | 8/2017 | Sniffin et al. | |

\* cited by examiner

SURGICAL INSTRUMENT

CROSS-REFERENCE TO RELATED APPLICATION

This application claims the benefit of Provisional Application No. 62/795,645, filed Jan. 23, 2019, which is incorporated herein by reference in its entirety for all purposes.

FIELD OF THE INVENTION

The invention relates generally to surgical instruments. Embodiments of the invention include long-shafted surgical instruments used for minimally invasive surgical procedures including but not limited to VATS (Video-Assisted Thoracoscopic Surgery) and MICS (Minimally Invasive Cardiac Surgery).

BACKGROUND

Surgical instruments such as, for example, those used for VATS (Video-Assisted Thoracoscopic Surgery) and MICS (Minimally Invasive Cardiac Surgery) are generally known and commercially available. There remains, however, a continuing need for improved surgical instruments. Instruments that provide enhanced functionality and efficacy would be especially desirable.

SUMMARY

Disclosed embodiments of the invention include improved surgical instruments that provide enhanced functionality, efficiency and efficacy. One example of an instrument includes (1) an elongated shaft including proximal and distal end portions, wherein the distal end portion has a first outer dimension, (2) a tool on a distal end portion of the shaft, wherein the tool is movable between first and second positions, (3) a handle on the proximal end portion of the shaft, wherein the handle includes an actuator, (4) a linkage coupling the actuator to the tool, to cause the tool to move between the first and second positions in response to actuation of the actuator, and wherein during operation of the instrument, an extending portion of the linkage extends beyond the first outer dimension of the distal end portion of the shaft, and (5) a shield on the distal end portion of the shaft and adjacent to the extending portion of the linkage, the shield having a dimension greater than the first outer dimension of the distal end portion of the shaft to cover the extending portion of the linkage that extends beyond the first outer dimension of the distal end portion of the shaft during operation of the instrument.

In embodiments, the shield has a radiused perimeter edge. The shield may include first and second sections on opposite sides of the shaft.

In embodiments, the distal end portion of the shaft has a second outer dimension about an axis perpendicular to the first outer dimension, and a distance between outer surfaces of the first and second sections of the shield is no greater than the second outer dimension. The first and second outer dimensions are the same in embodiments.

In embodiments, the instrument further comprises a pivot to pivotally connect the tool to the distal end portion of the shaft, and the linkage includes an arm coupled to the tool and the pivot, wherein the arm extends beyond the first outer dimension of the distal end portion of the shaft during operation of the instrument. The linkage may further include a rod extending through the shaft and including a proximal end coupled to the actuator and a distal end, and a cam coupling the distal end of the rod to the arm, wherein the cam extends beyond the first outer dimension of the distal end portion of the shaft during operation of the instrument.

In embodiments, the shield is configured (e.g., sized and shaped) to completely cover the extending portion of the linkage during operation of the instrument. For example, the shield is generally oval in shape in embodiments.

Embodiments of the instrument may include any one or more or all of the shield-related features described above Another example of an instrument comprises (1) an elongated shaft including proximal and distal end portions, (2) a tool on the distal end portion of the shaft, and (3) a handle on the proximal end portion of the shaft. The handle may include (4) a hand grip configured to be held by a hand of a user during operation of the instrument, (5) an actuator coupled to the tool, wherein the actuator is configured for actuation by the user when holding the hand grip, and (6) a counterweight on the handle proximal to the hand grip, wherein the counterweight is configured to locate a center of gravity of the instrument within the hand grip.

In embodiments, the hand grip includes proximal and distal ends defining a length, and
the counterweight is configured to locate the center of gravity of the instrument within a distal-most 50% of the length of the hand grip. In embodiments the hand grip includes proximal and distal ends defining a length, and the counterweight is configured to locate the center of gravity of the instrument within a distal-most 75% of the length of the hand grip.

In embodiments, the hand grip of the handle is formed of a first material having a first density, and the counterweight is formed of a second material having a second density that is greater than the first density of the first material. The elongated shaft includes the second material in embodiments.

In embodiments, the handle includes a housing comprising a void, and wherein the counterweight is located in the void. A fluid port on a proximal end of the housing is in fluid communication with the void, and a fluid channel through the counterweight fluidly couples the void to the elongated shaft, in embodiments. The fluid channel may include a tube.

In embodiments, the actuator includes a first member extending distally from the housing and configured for movement between first and second positions by squeezing motion of the hand of the user during operation of the instrument, and the hand grip includes a first grip portion on the first member. The first member is spring-biased to the first position, and is moved to the second position by the squeezing motion of the hand of the user during the operation of the instrument in embodiments. In embodiments, the actuator further includes a second member extending distally from the housing at a location spaced-apart from and generally parallel to the first member, and configured for movement between first and second positions by squeezing motion of the hand of the user during operation of the instrument, and the hand grip further includes a second grip portion on the second member, wherein the first and second members are configured such that the first and second grip portions are simultaneously gripped by the hand of the user during operation of the instrument.

Embodiments of the instrument may include any one or more or all of the counterweight-related features described above. Embodiments of the instrument may include any one or more or all of the shield-related features described above and any one or more or all of the counterweight-related features described above. Any or all of the instruments may be configured as a long-shafted or other minimally invasive surgical instrument (VATS/MICS).

DETAILED DESCRIPTION

Figure 1:
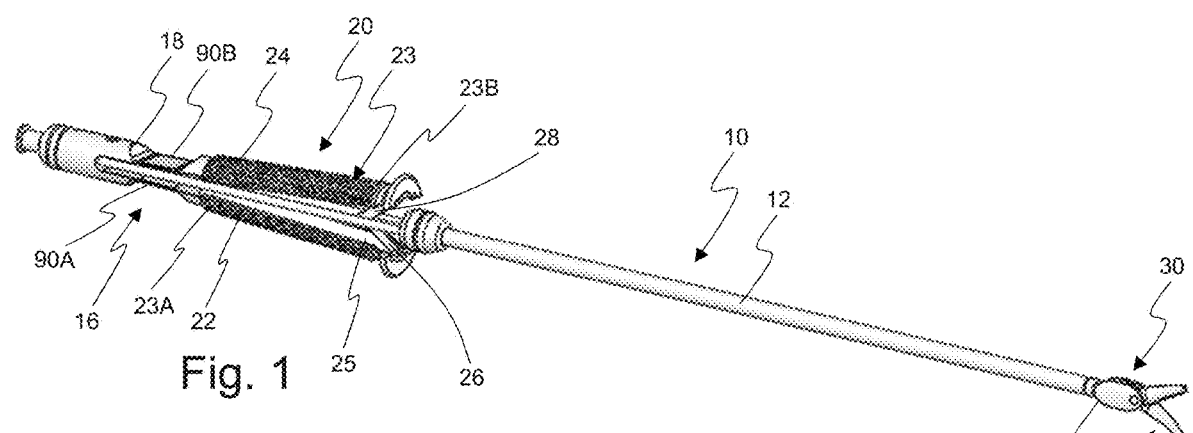
FIG. 1 is an isometric view of a surgical instrument in accordance with embodiments of the invention.

A surgical instrument 10 in accordance with embodiments of the invention is illustrated in FIG. 1. As shown, instrument 10 includes a shaft 12, a tool 14 on a distal end portion of the shaft, and a handle 16 on a proximal end portion of the shaft. Handle 16 includes a housing 18 and an actuator 20. In the illustrated embodiments, actuator 20 includes first and second members 22 and 24 extending distally from the housing 20. The first and second members 22 and 24 include portions 23A and 23B, respectively, that are configured to function as a hand grip 23 that can be held by the hand of a user during operation of the instrument 10. In the illustrated embodiments the members 22 and 24 are coupled to the tool 14 by a linkage 25 including arms 26 and 28. The members 22 and 24 are actuated when the user squeezes his or her hand to actuate the tool 14. As discussed in greater detail below, the instrument 10 also includes a shield 30 on the distal end portion of the shaft 12 to cover portions of the linkage 25 that extend beyond the outer dimension of the shaft during operation of the instrument. A counterweight (not visible in FIG. 1) in the handle 16 proximal to the hand grip 23 is configured to locate a center of gravity of the instrument 10 within the hand grip. Instrument 10 is shown as a VATS/MICS (Video-Assisted Thoracoscopic Surgery and Minimally Invasive Cardiac Surgery) device in FIG. 1, and includes a long shaft 12 (e.g., greater than six inches). Other embodiments of instrument 10 have shafts 12 with different (e.g., shorter) lengths, and/or are configured for other applications. Tool 14 is shown as a scissors in FIG. 1, but takes other forms such as, for example, a needle holder, forceps, valve rongeur or clamp, in other embodiments.

Figure 2A:
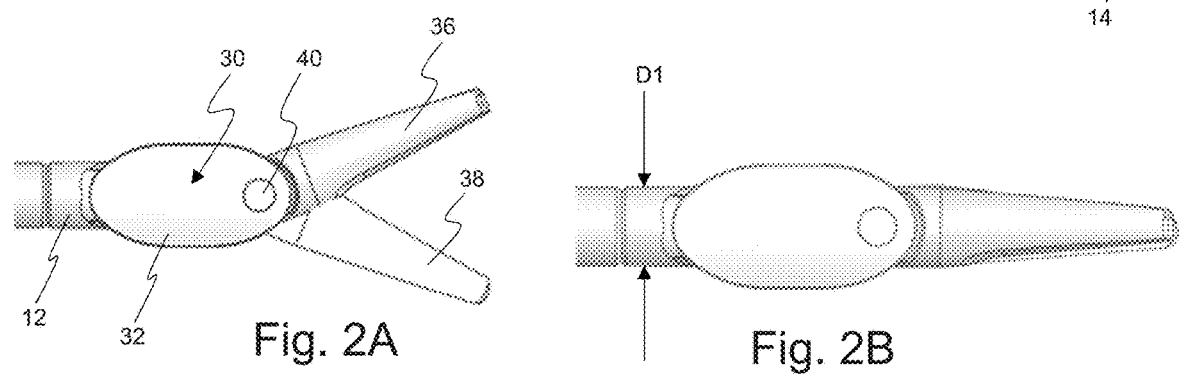
FIGS. 2A and 2B are detailed side views of the instrument shown in FIG. 1, with a tool of the instrument in a first (e.g., open or unactuated) state in FIG. 2A, and in a second (e.g., closed or actuated) state in FIG. 2B.
Figure 2B:
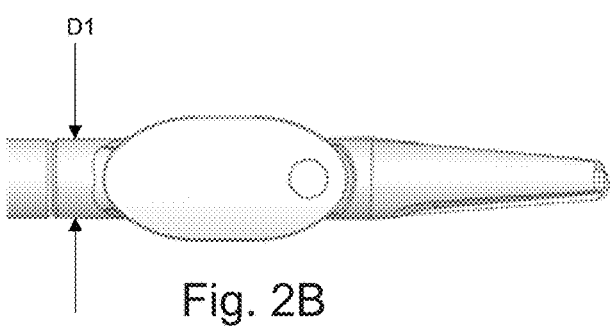
Figure 3A:
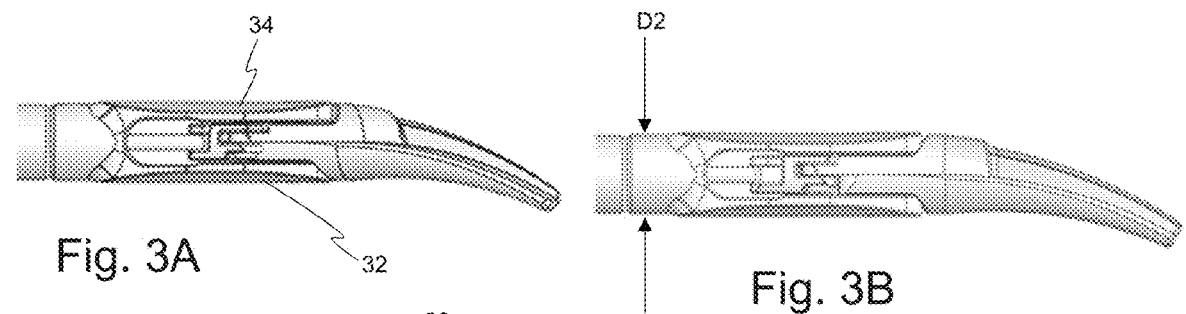
FIGS. 3A and 3B are detailed side views like those shown in FIGS. 2A and 2B, respectively, with a section of a shield removed to illustrate portions of a linkage coupling an actuator of the instrument to the tool.
Figure 3B:
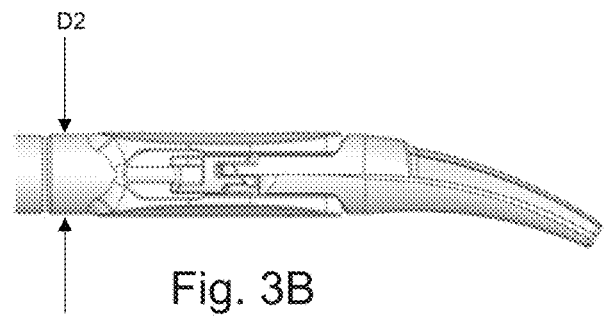

The distal end portion of the instrument 10, including the tool 14 and shield 30, can be described with reference to FIGS. 2A, 2B, 3A, 3B, 4A and 4B. Shaft 12 is an elongate tubular member having a distal end portion defining an outer dimension such as diameter D1 (when viewed from the sides as shown in FIG. 2B) and D2 (when viewed from the top or bottom as shown in FIG. 3B). In the illustrated embodiments shaft 12 has a generally circular cross section, and diameters D1 and D2 are the same. The illustrated embodiments of shield 30 include first and second sections 32 and 34. Proximal portions of the first and second sections 32 and 34 of the shield 30 are attached (e.g., by welding) to opposite sides of the distal end portion of the shaft 12. Tool 14, which is a scissors that includes blades 36 and 38 in the illustrated embodiment, is movable between a first position (e.g., an open or unactuated position, as shown in FIG. 2A) and a second position (e.g., a closed or actuated position, as shown in FIG. 2B). Blades 36 and 38 of the scissors are pivotally connected by a pin 40 to distal portions of the sections 32 and 34 of the shield 30. The linkage 25 coupling the scissors blades 36 and 38 to the actuator 20 (FIG. 1) includes rod 44, cams 46 and 48 and arms 50 and 52. Arms 50 and 52 are coupled to the blades 36 and 38, respectively, and extend proximally from the pin 40. Proximal ends of cams 46 and 48 are pivotally coupled to a distal end of rod 44 by pin 60. Distal ends of cams 46 and 48 are pivotally coupled to arms 50 and 52 by pins 62 and 64, respectively. Other embodiments of the invention can include other linkage structures.

Figure 4A:
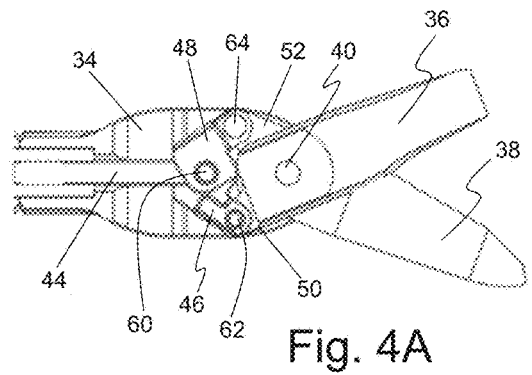
FIGS. 4A and 4B are detailed top views of the instrument shown in FIGS. 2A and 2B, respectively.
Figure 4B:
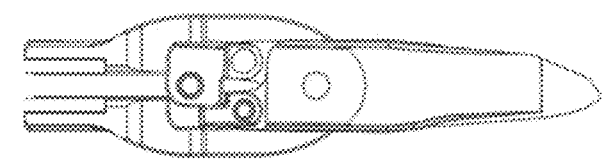
Figure 5:
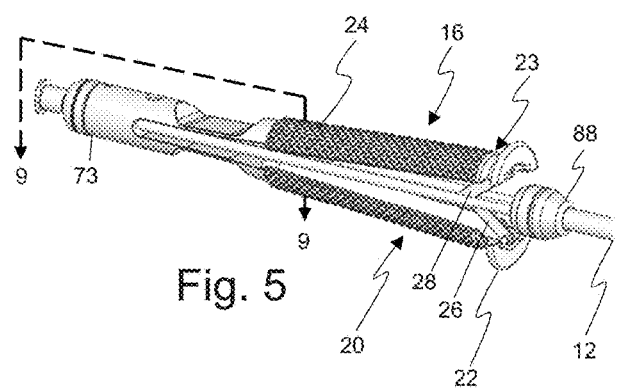
FIG. 5 is a detailed isometric view of the instrument shown in FIG. 1, illustrating a handle.
Figure 7:
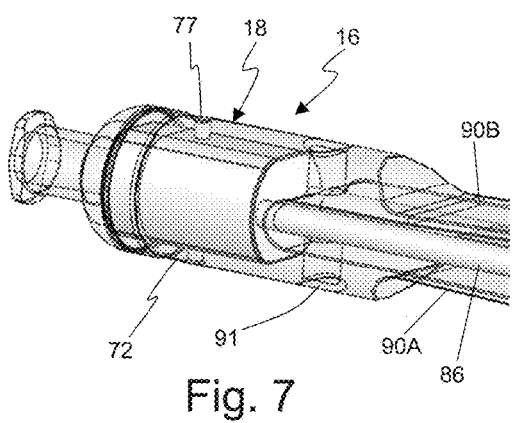
FIG. 7 is a detailed isometric view of the housing of the instrument shown in FIG. 6, with portions of the housing shown in phantom.

In response to the actuation of actuator 20 during the operation of instrument 10, rod 44 moves reciprocally along its longitudinal axis, and through the cams 46, 48 and arms 50, 52, causes the blades 36 and 38 to move between their open and closed positions. During this operation, portions of the linkage 25 extend beyond the outer dimension of the shaft 12. As shown in FIG. 4A, for example, when the blades 36 and 38 are in their open positions, portions of cams 46 and 48, and portions of arms 50 and 52, extend in directions perpendicular to the longitudinal axis of shaft 12 to positions that are beyond the diameter D1 of the shaft (e.g., when viewed from the side, portions of the linkage extend to heights above and below the shaft). Other embodiments of instrument 10 include a single-acting tool 14 (e.g., only one blade or other component moves in response to actuation of the actuator 20), and can have extending linkage portions that extend in only one direction beyond the diameter D1 (e.g., to a height only above or only below the shaft). Shield 30 is configured to shield those extending portions of the linkage 25 during operation of the instrument 10. In the illustrated embodiments, this function is provided by sizing and/or shaping the sections 32 and 34 of the shield 30 so their dimensions are greater than the diameter D1 of the shaft 12, and the sections cover the extending portions of the linkage 25 (e.g., when viewed from the sides). As shown in FIGS. 2A and 4A, for example, the size (i.e., height and width) of the sections 32 and 34 of the shield 30 (i.e., in a direction perpendicular to the longitudinal axis of the shaft 12) is a least as great as the size of the extending portions of the linkage 25 when the extending portions of the linkage are at the greatest extent of their movement during the operation of the instrument. The illustrated embodiments of the sections 32 and 34 of the shield 30 are generally oval in shape, and have radiused (i.e., rounded) perimeter edges. In the embodiments shown in FIGS. 3A and 3B, the shield 30 is configured to have dimensions generally equal to the diameter D2 of the shaft 12 in directions perpendicular to the directions of motion of the extending portions of linkage 25.

The proximal end portion of the instrument 10, including the handle 16 and counterweight 70, can be described with reference to FIGS. 5-10. The housing 18 of handle 16 includes a first section 72 with a proximal end 73 that opens into a hollow or void 74 that houses the counterweight 70, and a second section 76 attached to the proximal end of the first section to generally enclose the void. The illustrated embodiments of the instrument 12 include an opening 77 through the outer walls of the first section 72 of the housing 18 and the counterweight 70. A pin or other fastener (not shown) can be inserted into the opening 77 to secure the counterweight 70 within the void 74. Other embodiments include other structures and approaches for attaching the counterweight 70 to the handle 16.

Figure 8:
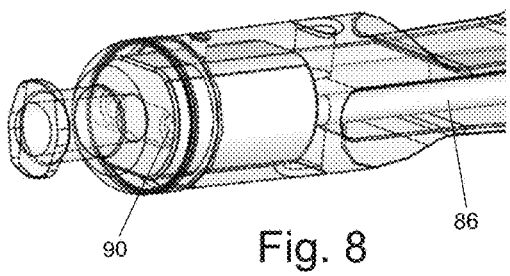
FIG. 8 is a detailed isometric view of the housing of the instrument shown in FIG. 6, with portions of the housing shown in phantom.
Figure 9:
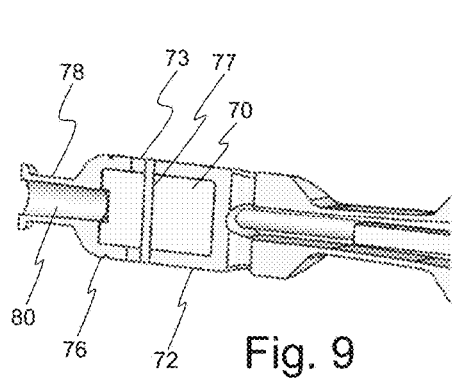
FIG. 9 is a detailed sectional view of the handle, taken along line 9-9 in FIG. 5.
Figure 10:
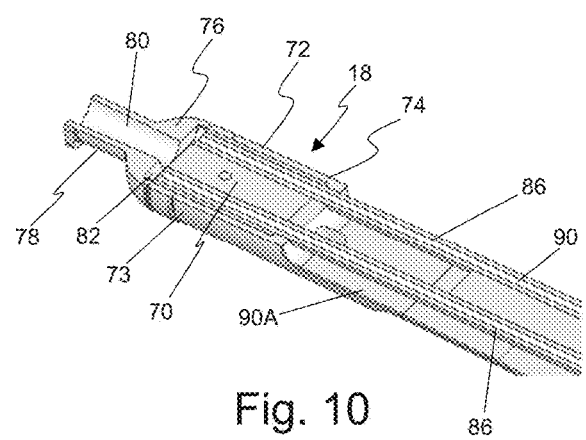
FIG. 10 is a detailed sectional view of the handle, taken along line 10-10 in FIG. 6.

A port 78 on a proximal end of the second section 76 defines a fluid pathway 80 into the void 74, and can be configured with a luer or other structure for connection to a source of saline or other fluid. As shown for example in FIG. 10, the void 74 in the housing 18 includes an open region 82 proximal to the counterweight 70. A pair of spaced-apart tubular rods 86 extend distally from the housing 18 to a hub 88 on a proximal end of the shaft 12 to mount the handle 16 to the shaft 12. As shown in FIGS. 8 and 10, for example, the rods 86 extend through the counterweight 70 and define fluid pathways 90 between the pathway 80 of the port 78 (via the open region 82 of the void 74 in the illustrated embodiments) and the hub 88. At hub 88 the fluid pathways 90 of the rods 86 are fluidly coupled to a tubular pathway within the shaft 12. Saline or other fluid applied to the instrument 10 through port 78 can thereby be delivered to the tool 14, for example to flush the tool and a surgical site during use of the instrument.

In the illustrated embodiments, the grip portions 23A and 23B of the members 22 and 24 of the actuator 20 are coupled to the distal end of the housing 18 by spring portions 90A and 90B, respectively. As shown, the members 22 and 24 are generally parallel to one another and to the longitudinal axis of the instrument 10, and are located on opposite sides of the rods 86 (e.g., on the top and bottom sides of the instrument) in the illustrated embodiments. Spring portions 90A and 90B bias the grip portions 23A and 23B, respectively, away from one other to a neutral or unactuated actuator position. Grip portions 23A and 23B are coupled to the rod 44 by arms 26 and 28, respectively. Tool 14 is driven to its actuated position (e.g., the blades 36 and 38 of the scissors are driven to the closed position) by squeezing the grip portions 23A and 23B toward one another to an actuated position. When the squeezing force on the grip portions 23A and 23B is released, the spring portions 90A and 90B return the grip portions to the unactuated position, and the tool is driven to its unactuated position (e.g., the blades of the scissors are driven to the open position). In the illustrated embodiments, the distal portion of the housing 18 includes ports 91 that extend through the housing into a region between the spring portions 90A and 90B of the actuator 20, to facilitate cleaning of the instrument 10. The grip portions 23A and 23B have textured surfaces in the illustrated embodiments.

Figure 6:
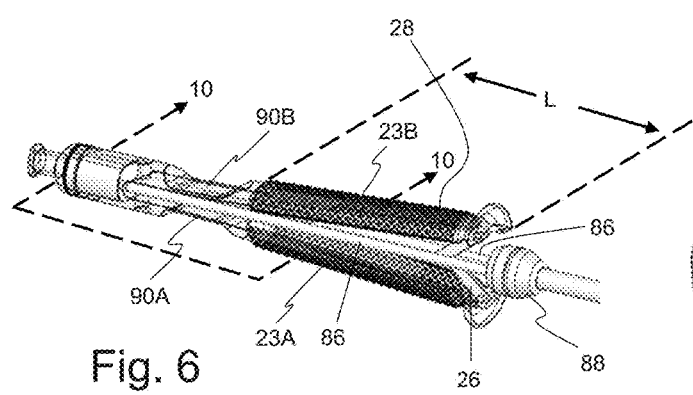
FIG. 6 is a detailed isometric view like that shown in FIG. 5, with portions of a housing of the handle shown in phantom.

As shown for example in FIG. 6, the grip portions 23A, 23B of the actuator 20 have proximal and distal ends and a length L. In embodiments, the instrument 10 is configured to locate its center of gravity along its longitudinal axis at a location within the grip portions 23A and 23B (i.e., at a location along the length L of the grip portions. In embodiments, the center of gravity is located closer to the distal ends of the grip portions 23A, 23B, than to the proximal ends (e.g., the center of gravity is located along the distal-most 50% of the length L of the grip portions. In other embodiments the center of gravity is located along the distal-most 75% of the length L of the grip portions 23A, 23B.

Any or all of one or more features of instrument 10, including the weight, size (e.g., length), density, materials of composition and relative locations of its components can be selected to configure the center of gravity at the desired location. For example, in embodiments, the housing 18 and actuator 20 are formed from a first material such as titanium having a first density, and other components such as shaft 12 and counterweight 70 are formed from a second material such as stainless steel that has a second density that is greater than the first density. In embodiments such as this, the size of the stainless steel counterweight 70, and the position of the counterweight proximal to the grip 23, can be selected to locate the center of gravity.

Instruments 10 in accordance with the disclosed embodiments offer a number of important advantages. Notably, they provide enhanced functionality and efficacy of use. The shield 30 minimizes trauma at the surgical site. The counterweight 70 enables the center of gravity of the instrument 10 to be located for enhanced ergonomics.

Although the invention has been described with reference to preferred embodiments, those of skill in the art will recognize that changes can be made in form a detail without departing from the spirit and scope of the invention. For example, although the illustrated embodiments include features associated with both the shield 30 and counterweight 70, other embodiments include features associated with the shield or counterweight, and not the other.

The invention claimed is:

1. A surgical instrument, comprising:
   an elongated shaft including proximal and distal end portions, wherein the distal end portion has a first outer dimension;
   a tool on a distal end portion of the shaft, wherein the tool is movable between first and second positions;
   a handle on the proximal end portion of the shaft, wherein the handle includes an actuator;
   a linkage coupling the actuator to the tool, to cause the tool to move between the first and second positions in response to actuation of the actuator, and wherein during operation of the instrument, an extending portion of the linkage extends beyond the first outer dimension of the distal end portion of the shaft; and
   a shield on the distal end portion of the shaft and adjacent to the extending portion of the linkage, the shield having a fixed dimension greater than the first outer dimension of the distal end portion of the shaft to cover the extending portion of the linkage that extends beyond the first outer dimension of the distal end portion of the shaft during operation of the instrument.

2. The surgical instrument of claim 1 wherein the shield has a radiused perimeter edge.

3. The surgical instrument of claim 1 wherein the shield includes first and second sections on opposite sides of the shaft.

4. The surgical instrument of claim 3 wherein:
   the distal end portion of the shaft has a second outer dimension about an axis perpendicular to the first outer dimension; and
   a distance between outer surfaces of the first and second sections of the shield is no greater than the second outer dimension.

5. The surgical instrument of claim 4 wherein the first and second outer dimensions are the same.

6. The surgical instrument of claim 1 wherein:
the instrument further comprises a pivot to pivotally connect the tool to the distal end portion of the shaft; and
the linkage includes an arm coupled to the tool and the pivot, wherein the arm extends beyond the first outer dimension of the distal end portion of the shaft during operation of the instrument.

7. The surgical instrument of claim 6 wherein the linkage further includes:
a rod extending through the shaft and including a proximal end coupled to the actuator and a distal end; and
a cam coupling the distal end of the rod to the arm, wherein the cam extends beyond the first outer dimension of the distal end portion of the shaft during operation of the instrument.

8. The surgical instrument of claim 1 wherein the shield is configured to completely cover the extending portion of the linkage during operation of the instrument.

9. The surgical instrument of claim 1 wherein the shield is generally oval in shape.

10. A surgical instrument, comprising: an elongated shaft including proximal and distal end portions; a tool on the distal end portion of the shaft; a handle on the proximal end portion of the shaft, including: a hand grip configured to be held by a hand of a user during operation of the instrument; and an actuator coupled to the tool, wherein the actuator is configured for actuation by the user when holding the hand grip; and a housing comprising a void; and a counterweight on the handle proximal to the hand grip and located in the void, wherein the counterweight is configured to locate a center of gravity of the instrument within the hand grip and a fluid port on a proximal end of the housing and in fluid communication with the void; and a fluid channel through the counterweight fluidly coupling the void to the elongated shaft.

11. The surgical instrument of claim 10 wherein:
the hand grip includes proximal and distal ends defining a length, and
the counterweight is configured to locate the center of gravity of the instrument within a distal-most 50% of the length of the hand grip.

12. The surgical instrument of claim 10 wherein:
the hand grip includes proximal and distal ends defining a length, and
the counterweight is configured to locate the center of gravity of the instrument within a distal-most 75% of the length of the hand grip.

13. The surgical instrument of claim 10 wherein:
the hand grip of the handle is formed of a first material having a first density; and
the counterweight is formed of a second material having a second density that is greater than the first density of the first material.

14. The surgical instrument of claim 13 wherein the elongated shaft includes the second material.

15. The surgical instrument of claim 10 wherein the fluid channel includes a tube.

16. The surgical instrument of claim 10 wherein:
the actuator includes a first member extending distally from the housing and configured for movement between first and second positions by squeezing motion of the hand of the user during operation of the instrument; and
the hand grip includes a first grip portion on the first member.

17. The surgical instrument of claim 16 wherein the first member is spring-biased to the first position, and is moved to the second position by the squeezing motion of the hand of the user during the operation of the instrument.

18. The surgical instrument of claim 16 wherein:
the actuator further includes a second member extending distally from the housing at a location spaced-apart from and generally parallel to the first member, and configured for movement between first and second positions by squeezing motion of the hand of the user during operation of the instrument; and
the hand grip further includes a second grip portion on the second member, wherein the first and second members are configured such that the first and second grip portions are simultaneously gripped by the hand of the user during operation of the instrument.

19. A surgical instrument, comprising: an elongated shaft including proximal and distal end portions, wherein the distal end portion has a first outer dimension; a tool on the distal end portion of the shaft, wherein the tool is movable between first and second positions; a handle on the proximal end portion of the shaft, wherein the handle includes: a hand grip configured to be held by a hand of a user during operation of the instrument; an actuator coupled to the tool, wherein the actuator is configured for actuation by the user when holding the hand grip; and a housing comprising a void; and a linkage coupling the actuator to the tool, to cause the tool to move between the first and second positions in response to actuation of the actuator, and wherein during operation of the instrument, an extending portion of the linkage extends beyond the first outer dimension of the distal end portion of the shaft; a shield on the distal end portion of the shaft and adjacent to the extending portion of the linkage, the shield having a fixed dimension greater than the first outer dimension of the distal end portion of the shaft to cover the extending portion of the linkage that extends beyond the first outer dimension of the distal end portion of the shaft during operation of the instrument; a counterweight on the handle proximal to the hand grip and located in the void, wherein the counterweight is configured to locate a center of gravity of the instrument within the hand grip.

20. A long-shafted minimally invasive surgical instrument in accordance with claim 19.

* * * * *